United States Patent [19]
Wolfman et al.

[11] Patent Number: 5,399,677
[45] Date of Patent: Mar. 21, 1995

[54] MUTANTS OF BONE MORPHOGENETIC PROTEINS

[75] Inventors: Neil M. Wolfman, Dover; John McCoy, Reading, both of Mass.

[73] Assignee: Genetics Institute, Inc., Cambridge, Mass.

[21] Appl. No.: 163,877

[22] Filed: Dec. 7, 1993

[51] Int. Cl.⁶ .................. C12N 15/12; C12N 15/18; A61K 37/36
[52] U.S. Cl. .................. 536/23.5; 536/23.51; 530/350; 530/399
[58] Field of Search .................. 536/23.5, 23.51; 530/350, 399

[56] References Cited

U.S. PATENT DOCUMENTS

| | | | |
|---|---|---|---|
| 5,013,649 | 5/1991 | Wang et al. | 435/69.1 |
| 5,106,748 | 4/1992 | Wozney et al. | 435/252.3 |
| 5,141,905 | 8/1992 | Rosen et al. | 435/69.1 |
| 5,187,076 | 2/1993 | Wozney et al. | 435/69.1 |

FOREIGN PATENT DOCUMENTS 114506 12/1989 European Pat. Off. .
433225 11/1991 European Pat. Off. .
WO91/18098 11/1991 WIPO .
WO93/00432 1/1993 WIPO .

OTHER PUBLICATIONS

Kohno, Meth. Enzym. 185:187–195 (1990).
Taniguchi et al., PNAS USA 77:5230–5233 (1980).
Thies et al., J. Bone and Mineral Res. 5(2);305 (1990).
Thies et al., Endocrinology, 130:1318–1324 (1992).
Sampath and Reddi, PNAS USA 80:6591–6595 (1983).
Norrander et al., Gene 26:101–106 (1983).
Sanger et al., J. Mol. Biol. 162:729–773 (1982).
Takagi et al., Nucl. Acids. Res. 13:2063–2074 (1985).
Dagert and Ehrlich, Gene 6:23 (1979).
Tandon and Horowitz, J. Biol. Chem., 262:4486–4491 (1987).

*Primary Examiner*—Garnette D. Draper
*Assistant Examiner*—Marianne Porta Allen
*Attorney, Agent, or Firm*—Steven R. Lazar; Thomas J. DesRosier

[57] ABSTRACT

DNA molecules encoding mutant forms of bone morphogenetic proteins (BMP) are disclosed, The mutant forms of BMP can be produced bacterially and refolded to produce biologically active homodimers or heterodimers of BMP. A method of making such mutant BMPs is also disclosed.

12 Claims, 1 Drawing Sheet

COMPARISON OF BMP SEQUENCES

| | | | | | | |
|---|---|---|---|---|---|---|
| BMP4 | | | | | SP | 2 |
| BMP5 | | | | NQNRNKSSSH | QDSSRMS | 17 |
| BMP6 | | | | QQSRNRSTQS | QDVARVS | 17 |
| BMP7 | | | STGSKQR | SQNRSKTPKN | QEALRMA | 24 |
| | | | | | | |
| BMP2 | QAKHKQRKRL | KSS CKRHPLY | VDFSDVGWND | WIVAPPGYHA | FYCHGECPFP | 50 |
| BMP4 | KHHSQRARKK | NKNCRRHSLY | VDFSDVGWND | WIVAPPGYQA | FYCHGDCPFP | 52 |
| BMP5 | SVGDYNTS EQ | KQACKKHELT | VSFRDLGWQD | WII APEGYAA | FYCDGECSFP | 67 |
| BMP6 | SAS DYNSS EL | KTACRKHELT | VSFQDLGWQD | WII APKGYAA | NYCDGECSFP | 67 |
| BMP7 | NVAENSS SDQ | RQACKKHELY | VSFRDLGWQD | WII APEGYAA | YYCEGECAFP | 74 |
| | | | | | | |
| BMP2 | LADHL NSTNH | AIVQTLVNSV | NSK.. I PKAC | CVPTELS AIS | MLYLDENEKV | 98 |
| BMP4 | LADHL NSTNH | AIVQTLVNSV | NSS.. I PKAC | CVPTELS AIS | MLYLDEYDKV | 100 |
| BMP5 | LNAHMNATNH | AIVQTLVHLM | FPDH.VPKPC | CAPTKLNAIS | VLYF DDSSNV | 116 |
| BMP6 | LNAHMNATNH | AIVQTLVHLM | NPEY.VPKPC | CAPTKLNAIS | VLYF DDNSNV | 116 |
| BMP7 | LNSYMNATNH | AIVQTLVHFI | NPET.VPKPC | CAPTQLNAIS | VLYF DDSSNV | 123 |
| | | | | | | |
| BMP2 | VLKNYQDMVV | EG. CGCR | | | | 114 |
| BMP4 | VLKNYQEMVV | EG. CGCR | | | | 116 |
| BMP5 | I LKKYRNMVV | RS. CGCH | | | | 132 |
| BMP6 | I LKKYRNMVV | RA. CGCH | | | | 132 |
| BMP7 | I LKKYRNMVV | RA. CGCH | | | | 139 |

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 342 base pairs
( B ) TYPE: nucleic acid
( C ) STRANDEDNESS: double
( D ) TOPOLOGY: unknown ( i i ) MOLECULE TYPE: DNA (genomic)

( v i ) ORIGINAL SOURCE:
( A ) ORGANISM: bmp-2

( i x ) FEATURE:
( A ) NAME/KEY: CDS
( B ) LOCATION: 1..342

( x i ) SEQUENCE DESCRIPTION: SEQ ID NO:1:

```
CAA GCC AAA CAC AAA CAG CGG AAA CGC CTT AAG TCC AGC TGT AAG AGA      48
Gln Ala Lys His Lys Gln Arg Lys Arg Leu Lys Ser Ser Cys Lys Arg
 1               5                  10                  15

CAC CCT TTG TAC GTG GAC TTC AGT GAC GTG GGG TGG AAT GAC TGG ATT      96
His Pro Leu Tyr Val Asp Phe Ser Asp Val Gly Trp Asn Asp Trp Ile
                20                  25                  30

GTG GCT CCC CCG GGG TAT CAC GCC TTT TAC TGC CAC GGA GAA TGC CCT     144
Val Ala Pro Pro Gly Tyr His Ala Phe Tyr Cys His Gly Glu Cys Pro
             35                  40                  45

TTT CCT CTG GCT GAT CAT CTG AAC TCC ACT AAT CAT GCC ATT GTT CAG     192
Phe Pro Leu Ala Asp His Leu Asn Ser Thr Asn His Ala Ile Val Gln
         50                  55                  60

ACG TTG GTC AAC TCT GTT AAC TCT AAG ATT CCT AAG GCA TGC TGT GTC     240
Thr Leu Val Asn Ser Val Asn Ser Lys Ile Pro Lys Ala Cys Cys Val
 65                  70                  75                  80

CCG ACA GAA CTC AGT GCT ATC TCG ATG CTG TAC CTT GAC GAG AAT GAA     288
Pro Thr Glu Leu Ser Ala Ile Ser Met Leu Tyr Leu Asp Glu Asn Glu
                 85                  90                  95
```

| | | | | | | | | | | | | | | | | |
|---|---|---|---|---|---|---|---|---|---|---|---|---|---|---|---|---|
| AAG | GTT | GTA | TTA | AAG | AAC | TAT | CAG | GAC | ATG | GTT | GTG | GAG | GGT | TGT | GGG | 336 |
| Lys | Val | Val | Leu | Lys | Asn | Tyr | Gln | Asp | Met | Val | Val | Glu | Gly | Cys | Gly | |
| | | | 100 | | | | | 105 | | | | | 110 | | | |

| | | |
|---|---|---|
| TGT | CGC | 342 |
| Cys | Arg | |

(2) INFORMATION FOR SEQ ID NO:2:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Gln | Ala | Lys | His | Lys | Gln | Arg | Lys | Arg | Leu | Lys | Ser | Ser | Cys | Lys | Arg |
| 1 | | | | 5 | | | | | 10 | | | | | 15 |
| His | Pro | Leu | Tyr | Val | Asp | Phe | Ser | Asp | Val | Gly | Trp | Asn | Asp | Trp | Ile |
| | | | 20 | | | | 25 | | | | | 30 | | | |
| Val | Ala | Pro | Pro | Gly | Tyr | His | Ala | Phe | Tyr | Cys | His | Gly | Glu | Cys | Pro |
| | | 35 | | | | 40 | | | | | 45 | | | | |
| Phe | Pro | Leu | Ala | Asp | His | Leu | Asn | Ser | Thr | Asn | His | Ala | Ile | Val | Gln |
| | 50 | | | | 55 | | | | | 60 | | | | | |
| Thr | Leu | Val | Asn | Ser | Val | Asn | Ser | Lys | Ile | Pro | Lys | Ala | Cys | Cys | Val |
| 65 | | | | 70 | | | | 75 | | | | | 80 | | |
| Pro | Thr | Glu | Leu | Ser | Ala | Ile | Ser | Met | Leu | Tyr | Leu | Asp | Glu | Asn | Glu |
| | | | | 85 | | | | 90 | | | | | 95 | | |
| Lys | Val | Val | Leu | Lys | Asn | Tyr | Gln | Asp | Met | Val | Val | Glu | Gly | Cys | Gly |
| | | | 100 | | | | | 105 | | | | | 110 | | |

Cys Arg (2) INFORMATION FOR SEQ ID NO:3:

(i) SEQUENCE CHARACTERISTICS:
        (A) LENGTH: 348 base pairs
        (B) TYPE: nucleic acid
        (C) STRANDEDNESS: double
        (D) TOPOLOGY: unknown (ii) MOLECULE TYPE: DNA (genomic)

(vi) ORIGINAL SOURCE:
        (A) ORGANISM: bmp-4

(ix) FEATURE:
        (A) NAME/KEY: CDS
        (B) LOCATION: 1..348

(xi) SEQUENCE DESCRIPTION: SEQ ID NO:3:

| | | | | | | | | | | | | | | | | |
|---|---|---|---|---|---|---|---|---|---|---|---|---|---|---|---|---|
| AGC | CCT | AAG | CAT | CAC | TCA | CAG | CGG | GCC | AGG | AAG | AAG | AAT | AAG | AAC | TGC | 48 |
| Ser | Pro | Lys | His | His | Ser | Gln | Arg | Ala | Arg | Lys | Lys | Asn | Lys | Asn | Cys | |
| 1 | | | | 5 | | | | | 10 | | | | | 15 | | |
| CGG | CGC | CAC | TCG | CTC | TAT | GTG | GAC | TTC | AGC | GAT | GTG | GGC | TGG | AAT | GAC | 96 |
| Arg | Arg | His | Ser | Leu | Tyr | Val | Asp | Phe | Ser | Asp | Val | Gly | Trp | Asn | Asp | |
| | | | 20 | | | | | 25 | | | | | 30 | | | |
| TGG | ATT | GTG | GCC | CCA | CCA | GGC | TAC | CAG | GCC | TTC | TAC | TGC | CAT | GGG | GAC | 144 |
| Trp | Ile | Val | Ala | Pro | Pro | Gly | Tyr | Gln | Ala | Phe | Tyr | Cys | His | Gly | Asp | |
| | | | 35 | | | | | 40 | | | | | 45 | | | |
| TGC | CCC | TTT | CCA | CTG | GCT | GAC | CAC | CTC | AAC | TCA | ACC | AAC | CAT | GCC | ATT | 192 |
| Cys | Pro | Phe | Pro | Leu | Ala | Asp | His | Leu | Asn | Ser | Thr | Asn | His | Ala | Ile | |
| | | 50 | | | | | 55 | | | | | 60 | | | | |
| GTG | CAG | ACC | CTG | GTC | AAT | TCT | GTC | AAT | TCC | AGT | ATC | CCC | AAA | GCC | TGT | 240 |
| Val | Gln | Thr | Leu | Val | Asn | Ser | Val | Asn | Ser | Ser | Ile | Pro | Lys | Ala | Cys | |
| 65 | | | | 70 | | | | | 75 | | | | | 80 | | |

```
TGT GTG CCC ACT GAA CTG AGT GCC ATC TCC ATG CTG TAC CTG GAT GAG      288
Cys Val Pro Thr Glu Leu Ser Ala Ile Ser Met Leu Tyr Leu Asp Glu
             85                  90                  95

TAT GAT AAG GTG GTA CTG AAA AAT TAT CAG GAG ATG GTA GTA GAG GGA      336
Tyr Asp Lys Val Val Leu Lys Asn Tyr Gln Glu Met Val Val Glu Gly
            100                 105                 110

TGT GGG TGC CGC                                                       348
Cys Gly Cys Arg
            115
```

(2) INFORMATION FOR SEQ ID NO:4:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO:4:

```
Ser Pro Lys His His Ser Gln Arg Ala Arg Lys Lys Asn Lys Asn Cys
 1               5                  10                  15

Arg Arg His Ser Leu Tyr Val Asp Phe Ser Asp Val Gly Trp Asn Asp
            20                  25                  30

Trp Ile Val Ala Pro Pro Gly Tyr Gln Ala Phe Tyr Cys His Gly Asp
            35                  40                  45

Cys Pro Phe Pro Leu Ala Asp His Leu Asn Ser Thr Asn His Ala Ile
 50                  55                  60

Val Gln Thr Leu Val Asn Ser Val Asn Ser Ser Ile Pro Lys Ala Cys
 65                  70                  75                  80

Cys Val Pro Thr Glu Leu Ser Ala Ile Ser Met Leu Tyr Leu Asp Glu
             85                  90                  95

Tyr Asp Lys Val Val Leu Lys Asn Tyr Gln Glu Met Val Val Glu Gly
            100                 105                 110

Cys Gly Cys Arg
            115
```

(2) INFORMATION FOR SEQ ID NO:5:

(i) SEQUENCE CHARACTERISTICS:
        (A) LENGTH: 396 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: bmp-5

(ix) FEATURE:
        (A) NAME/KEY: CDS
        (B) LOCATION: 1..396

(xi) SEQUENCE DESCRIPTION: SEQ ID NO:5:

```
AAT CAA AAC CGC AAT AAA TCC AGC TCT CAT CAG GAC TCC TCC AGA ATG       48
Asn Gln Asn Arg Asn Lys Ser Ser Ser His Gln Asp Ser Ser Arg Met
 1               5                  10                  15

TCC AGT GTT GGA GAT TAT AAC ACA AGT GAG CAA AAA CAA GCC TGT AAG       96
Ser Ser Val Gly Asp Tyr Asn Thr Ser Glu Gln Lys Gln Ala Cys Lys
            20                  25                  30

AAG CAC GAA CTC TAT GTG AGC TTC CGG GAT CTG GGA TGG CAG GAC TGG      144
Lys His Glu Leu Tyr Val Ser Phe Arg Asp Leu Gly Trp Gln Asp Trp
            35                  40                  45

ATT ATA GCA CCA GAA GGA TAC GCT GCA TTT TAT TGT GAT GGA GAA TGT      192
Ile Ile Ala Pro Glu Gly Tyr Ala Ala Phe Tyr Cys Asp Gly Glu Cys
```

|     |     |     |     | 50  |     |     |     |     | 55  |     |     |     |     | 60  |     |     |
|-----|-----|-----|-----|-----|-----|-----|-----|-----|-----|-----|-----|-----|-----|-----|-----|-----|
| TCT | TTT | CCA | CTT | AAC | GCC | CAT | ATG | AAT | GCC | ACC | AAC | CAC | GCT | ATA | GTT | 240 |
| Ser | Phe | Pro | Leu | Asn | Ala | His | Met | Asn | Ala | Thr | Asn | His | Ala | Ile | Val |     |
| 65  |     |     |     | 70  |     |     |     |     | 75  |     |     |     |     |     | 80  |     |
| CAG | ACT | CTG | GTT | CAT | CTG | ATG | TTT | CCT | GAC | CAC | GTA | CCA | AAG | CCT | TGT | 288 |
| Gln | Thr | Leu | Val | His | Leu | Met | Phe | Pro | Asp | His | Val | Pro | Lys | Pro | Cys |     |
|     |     |     |     | 85  |     |     |     |     | 90  |     |     |     |     | 95  |     |     |
| TGT | GCT | CCA | ACC | AAA | TTA | AAT | GCC | ATC | TCT | GTT | CTG | TAC | TTT | GAT | GAC | 336 |
| Cys | Ala | Pro | Thr | Lys | Leu | Asn | Ala | Ile | Ser | Val | Leu | Tyr | Phe | Asp | Asp |     |
|     |     |     | 100 |     |     |     |     | 105 |     |     |     |     | 110 |     |     |     |
| AGC | TCC | AAT | GTC | ATT | TTG | AAA | AAA | TAT | AGA | AAT | ATG | GTA | GTA | CGC | TCA | 384 |
| Ser | Ser | Asn | Val | Ile | Leu | Lys | Lys | Tyr | Arg | Asn | Met | Val | Val | Arg | Ser |     |
|     |     | 115 |     |     |     |     | 120 |     |     |     |     | 125 |     |     |     |     |
| TGT | GGC | TGC | CAC |     |     |     |     |     |     |     |     |     |     |     |     | 396 |
| Cys | Gly | Cys | His |     |     |     |     |     |     |     |     |     |     |     |     |     |
|     |     | 130 |     |     |     |     |     |     |     |     |     |     |     |     |     |     |

( 2 ) INFORMATION FOR SEQ ID NO:6:

( i ) SEQUENCE CHARACTERISTICS:
        ( A ) LENGTH: 132 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Asn | Gln | Asn | Arg | Asn | Lys | Ser | Ser | Ser | His | Gln | Asp | Ser | Ser | Arg | Met |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Ser | Val | Gly | Asp | Tyr | Asn | Thr | Ser | Glu | Gln | Lys | Gln | Ala | Cys | Lys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Lys | His | Glu | Leu | Tyr | Val | Ser | Phe | Arg | Asp | Leu | Gly | Trp | Gln | Asp | Trp |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ile | Ile | Ala | Pro | Glu | Gly | Tyr | Ala | Ala | Phe | Tyr | Cys | Asp | Gly | Glu | Cys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Phe | Pro | Leu | Asn | Ala | His | Met | Asn | Ala | Thr | Asn | His | Ala | Ile | Val |
|-----|-----|-----|-----|-----|-----|-----|-----|-----|-----|-----|-----|-----|-----|-----|-----|
| 65  |     |     |     | 70  |     |     |     |     | 75  |     |     |     |     |     | 80  |

| Gln | Thr | Leu | Val | His | Leu | Met | Phe | Pro | Asp | His | Val | Pro | Lys | Pro | Cys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Cys | Ala | Pro | Thr | Lys | Leu | Asn | Ala | Ile | Ser | Val | Leu | Tyr | Phe | Asp | Asp |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ser | Ser | Asn | Val | Ile | Leu | Lys | Lys | Tyr | Arg | Asn | Met | Val | Val | Arg | Ser |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Cys | Gly | Cys | His |
|-----|-----|-----|-----|
|     |     | 130 |     |

( 2 ) INFORMATION FOR SEQ ID NO:7:

( i ) SEQUENCE CHARACTERISTICS:
        ( A ) LENGTH: 406 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: bmp-6

( i x ) FEATURE:
        ( A ) NAME/KEY: CDS
        ( B ) LOCATION: 1..396

( x i ) SEQUENCE DESCRIPTION: SEQ ID NO:7:

| CAA | CAG | AGT | CGT | AAT | CGC | TCT | ACC | CAG | TCC | CAG | GAC | GTG | GCG | CGG | GTC | 48 |
|-----|-----|-----|-----|-----|-----|-----|-----|-----|-----|-----|-----|-----|-----|-----|-----|----|

|  | Gln<br>1 | Gln | Ser | Arg | Asn<br>5 | Arg | Ser | Thr | Gln | Ser<br>10 | Gln | Asp | Val | Ala | Arg<br>15 | Val |  |
|---|---|---|---|---|---|---|---|---|---|---|---|---|---|---|---|---|---|
|  | TCC<br>Ser | AGT<br>Ser | GCT<br>Ala | TCA<br>Ser<br>20 | GAT<br>Asp | TAC<br>Tyr | AAC<br>Asn | AGC<br>Ser | AGT<br>Ser<br>25 | GAA<br>Glu | TTG<br>Leu | AAA<br>Lys | ACA<br>Thr | GCC<br>Ala<br>30 | TGC<br>Cys | AGG<br>Arg | 96 |
|  | AAG<br>Lys | CAT<br>His | GAG<br>Glu<br>35 | CTG<br>Leu | TAT<br>Tyr | GTG<br>Val | AGT<br>Ser | TTC<br>Phe<br>40 | CAA<br>Gln | GAC<br>Asp | CTG<br>Leu | GGA<br>Gly | TGG<br>Trp<br>45 | CAG<br>Gln | GAC<br>Asp | TGG<br>Trp | 144 |
|  | ATC<br>Ile | ATT<br>Ile | GCA<br>Ala<br>50 | CCC<br>Pro | AAG<br>Lys | GGC<br>Gly | TAT<br>Tyr | GCT<br>Ala<br>55 | GCC<br>Ala | AAT<br>Asn | TAC<br>Tyr | TGT<br>Cys | GAT<br>Asp<br>60 | GGA<br>Gly | GAA<br>Glu | TGC<br>Cys | 192 |
|  | TCC<br>Ser<br>65 | TTC<br>Phe | CCA<br>Pro | CTC<br>Leu | AAC<br>Asn | GCA<br>Ala<br>70 | CAC<br>His | ATG<br>Met | AAT<br>Asn | GCA<br>Ala | ACC<br>Thr<br>75 | AAC<br>Asn | CAC<br>His | GCG<br>Ala | ATT<br>Ile | GTG<br>Val<br>80 | 240 |
|  | CAG<br>Gln | ACC<br>Thr | TTG<br>Leu | GTT<br>Val | CAC<br>His<br>85 | CTT<br>Leu | ATG<br>Met | AAC<br>Asn | CCC<br>Pro | GAG<br>Glu<br>90 | TAT<br>Tyr | GTC<br>Val | CCC<br>Pro | AAA<br>Lys<br>95 | CCG<br>Pro | TGC<br>Cys | 288 |
|  | TGT<br>Cys | GCG<br>Ala | CCA<br>Pro | ACT<br>Thr<br>100 | AAG<br>Lys | CTA<br>Leu | AAT<br>Asn | GCC<br>Ala | ATC<br>Ile<br>105 | TCG<br>Ser | GTT<br>Val | CTT<br>Leu | TAC<br>Tyr | TTT<br>Phe<br>110 | GAT<br>Asp | GAC<br>Asp | 336 |
|  | AAC<br>Asn | TCC<br>Ser | AAT<br>Asn<br>115 | GTC<br>Val | ATT<br>Ile | CTG<br>Leu | AAA<br>Lys | AAA<br>Lys<br>120 | TAC<br>Tyr | AGG<br>Arg | AAT<br>Asn | ATG<br>Met | GTT<br>Val<br>125 | GTA<br>Val | AGA<br>Arg | GCT<br>Ala | 384 |
|  | TGT<br>Cys | GGA<br>Gly | TGC<br>Cys | CAC<br>His<br>130 | TAACTCGAAA |  |  |  |  |  |  |  |  |  |  |  | 406 |

( 2 ) INFORMATION FOR SEQ ID NO:8:

( i ) SEQUENCE CHARACTERISTICS:
        ( A ) LENGTH: 132 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Gln<br>1 | Gln | Ser | Arg | Asn<br>5 | Arg | Ser | Thr | Gln | Ser<br>10 | Gln | Asp | Val | Ala | Arg<br>15 | Val |
|---|---|---|---|---|---|---|---|---|---|---|---|---|---|---|---|
| Ser | Ser | Ala | Ser<br>20 | Asp | Tyr | Asn | Ser | Ser<br>25 | Glu | Leu | Lys | Thr | Ala<br>30 | Cys | Arg |
| Lys | His | Glu<br>35 | Leu | Tyr | Val | Ser | Phe<br>40 | Gln | Asp | Leu | Gly | Trp<br>45 | Gln | Asp | Trp |
| Ile | Ile | Ala<br>50 | Pro | Lys | Gly | Tyr | Ala<br>55 | Ala | Asn | Tyr | Cys | Asp<br>60 | Gly | Glu | Cys |
| Ser<br>65 | Phe | Pro | Leu | Asn | Ala<br>70 | His | Met | Asn | Ala | Thr<br>75 | Asn | His | Ala | Ile | Val<br>80 |
| Gln | Thr | Leu | Val | His<br>85 | Leu | Met | Asn | Pro | Glu<br>90 | Tyr | Val | Pro | Lys<br>95 | Pro | Cys |
| Cys | Ala | Pro | Thr<br>100 | Lys | Leu | Asn | Ala | Ile<br>105 | Ser | Val | Leu | Tyr | Phe<br>110 | Asp | Asp |
| Asn | Ser | Asn<br>115 | Val | Ile | Leu | Lys | Lys<br>120 | Tyr | Arg | Asn | Met | Val<br>125 | Val | Arg | Ala |
| Cys | Gly | Cys | His<br>130 |

( 2 ) INFORMATION FOR SEQ ID NO:9:

( i ) SEQUENCE CHARACTERISTICS:
        ( A ) LENGTH: 417 base pairs
        ( B ) TYPE: nucleic acid
        ( C ) STRANDEDNESS: double
        ( D ) TOPOLOGY: linear (i i) MOLECULE TYPE: DNA (genomic)

(v i) ORIGINAL SOURCE:
    (A) ORGANISM: bmp-7

(i x) FEATURE:
    (A) NAME/KEY: CDS
    (B) LOCATION: 1..417

(x i) SEQUENCE DESCRIPTION: SEQ ID NO:9:

| TCC | ACG | GGG | AGC | AAA | CAG | CGC | AGC | CAG | AAC | CGC | TCC | AAG | ACG | CCC | AAG | 48 |
|---|---|---|---|---|---|---|---|---|---|---|---|---|---|---|---|---|
| Ser | Thr | Gly | Ser | Lys | Gln | Arg | Ser | Gln | Asn | Arg | Ser | Lys | Thr | Pro | Lys | |
| 1 | | | | 5 | | | | | 10 | | | | | 15 | | |

| AAC | CAG | GAA | GCC | CTG | CGG | ATG | GCC | AAC | GTG | GCA | GAG | AAC | AGC | AGC | AGC | 96 |
|---|---|---|---|---|---|---|---|---|---|---|---|---|---|---|---|---|
| Asn | Gln | Glu | Ala | Leu | Arg | Met | Ala | Asn | Val | Ala | Glu | Asn | Ser | Ser | Ser | |
| | | | 20 | | | | | 25 | | | | | 30 | | | |

| GAC | CAG | AGG | CAG | GCC | TGT | AAG | AAG | CAC | GAG | CTG | TAT | GTC | AGC | TTC | CGA | 144 |
|---|---|---|---|---|---|---|---|---|---|---|---|---|---|---|---|---|
| Asp | Gln | Arg | Gln | Ala | Cys | Lys | Lys | His | Glu | Leu | Tyr | Val | Ser | Phe | Arg | |
| | | 35 | | | | | 40 | | | | | 45 | | | | |

| GAC | CTG | GGC | TGG | CAG | GAC | TGG | ATC | ATC | GCG | CCT | GAA | GGC | TAC | GCC | GCC | 192 |
|---|---|---|---|---|---|---|---|---|---|---|---|---|---|---|---|---|
| Asp | Leu | Gly | Trp | Gln | Asp | Trp | Ile | Ile | Ala | Pro | Glu | Gly | Tyr | Ala | Ala | |
| | | 50 | | | | 55 | | | | | 60 | | | | | |

| TAC | TAC | TGT | GAG | GGG | GAG | TGT | GCC | TTC | CCT | CTG | AAC | TCC | TAC | ATG | AAC | 240 |
|---|---|---|---|---|---|---|---|---|---|---|---|---|---|---|---|---|
| Tyr | Tyr | Cys | Glu | Gly | Glu | Cys | Ala | Phe | Pro | Leu | Asn | Ser | Tyr | Met | Asn | |
| 65 | | | | | 70 | | | | | 75 | | | | | 80 | |

| GCC | ACC | AAC | CAC | GCC | ATC | GTG | CAG | ACG | CTG | GTC | CAC | TTC | ATC | AAC | CCG | 288 |
|---|---|---|---|---|---|---|---|---|---|---|---|---|---|---|---|---|
| Ala | Thr | Asn | His | Ala | Ile | Val | Gln | Thr | Leu | Val | His | Phe | Ile | Asn | Pro | |
| | | | | 85 | | | | | 90 | | | | | 95 | | |

| GAA | ACG | GTG | CCC | AAG | CCC | TGC | TGT | GCG | CCC | ACG | CAG | CTC | AAT | GCC | ATC | 336 |
|---|---|---|---|---|---|---|---|---|---|---|---|---|---|---|---|---|
| Glu | Thr | Val | Pro | Lys | Pro | Cys | Cys | Ala | Pro | Thr | Gln | Leu | Asn | Ala | Ile | |
| | | | 100 | | | | 105 | | | | | 110 | | | | |

| TCC | GTC | CTC | TAC | TTC | GAT | GAC | AGC | TCC | AAC | GTC | ATC | CTG | AAG | AAA | TAC | 384 |
|---|---|---|---|---|---|---|---|---|---|---|---|---|---|---|---|---|
| Ser | Val | Leu | Tyr | Phe | Asp | Asp | Ser | Ser | Asn | Val | Ile | Leu | Lys | Lys | Tyr | |
| | | 115 | | | | | 120 | | | | | 125 | | | | |

| AGA | AAC | ATG | GTG | GTC | CGG | GCC | TGT | GGC | TGC | CAC | | | | | | 417 |
|---|---|---|---|---|---|---|---|---|---|---|---|---|---|---|---|---|
| Arg | Asn | Met | Val | Val | Arg | Ala | Cys | Gly | Cys | His | | | | | | |
| | 130 | | | | | 135 | | | | | | | | | | |

(2) INFORMATION FOR SEQ ID NO:10:

(i) SEQUENCE CHARACTERISTICS:
        (A) LENGTH: 139 amino acids
        (B) TYPE: amino acid
        (D) TOPOLOGY: linear (i i) MOLECULE TYPE: protein (x i) SEQUENCE DESCRIPTION: SEQ ID NO:10:

| Ser | Thr | Gly | Ser | Lys | Gln | Arg | Ser | Gln | Asn | Arg | Ser | Lys | Thr | Pro | Lys |
|---|---|---|---|---|---|---|---|---|---|---|---|---|---|---|---|
| 1 | | | | 5 | | | | | 10 | | | | | 15 | |

| Asn | Gln | Glu | Ala | Leu | Arg | Met | Ala | Asn | Val | Ala | Glu | Asn | Ser | Ser | Ser |
|---|---|---|---|---|---|---|---|---|---|---|---|---|---|---|---|
| | | | 20 | | | | | 25 | | | | | 30 | | |

| Asp | Gln | Arg | Gln | Ala | Cys | Lys | Lys | His | Glu | Leu | Tyr | Val | Ser | Phe | Arg |
|---|---|---|---|---|---|---|---|---|---|---|---|---|---|---|---|
| | | 35 | | | | | 40 | | | | | 45 | | | |

| Asp | Leu | Gly | Trp | Gln | Asp | Trp | Ile | Ile | Ala | Pro | Glu | Gly | Tyr | Ala | Ala |
|---|---|---|---|---|---|---|---|---|---|---|---|---|---|---|---|
| | | 50 | | | | 55 | | | | | 60 | | | | |

| Tyr | Tyr | Cys | Glu | Gly | Glu | Cys | Ala | Phe | Pro | Leu | Asn | Ser | Tyr | Met | Asn |
|---|---|---|---|---|---|---|---|---|---|---|---|---|---|---|---|
| 65 | | | | | 70 | | | | | 75 | | | | | 80 |

| Ala | Thr | Asn | His | Ala | Ile | Val | Gln | Thr | Leu | Val | His | Phe | Ile | Asn | Pro |
|---|---|---|---|---|---|---|---|---|---|---|---|---|---|---|---|
| | | | | 85 | | | | | 90 | | | | | 95 | |

| Glu | Thr | Val | Pro | Lys | Pro | Cys | Cys | Ala | Pro | Thr | Gln | Leu | Asn | Ala | Ile |
|---|---|---|---|---|---|---|---|---|---|---|---|---|---|---|---|
| | | | 100 | | | | 105 | | | | | 110 | | | |

| Ser | Val | Leu | Tyr | Phe | Asp | Asp | Ser | Ser | Asn | Val | Ile | Leu | Lys | Lys | Tyr |
|---|---|---|---|---|---|---|---|---|---|---|---|---|---|---|---|

```
                    115                      120                          125
Arg  Asn  Met  Val  Val  Arg  Ala  Cys  Gly  Cys  His
         130                      135
```

MUTANTS OF BONE MORPHOGENETIC PROTEINS

The present invention relates to mutants of bone morphogenetic proteins. These mutants are useful, particularly for use in improved processes for preparation of biologically active dimeric recombinant bone morphogenetic proteins produced in insoluble form from bacterial cell cultures.

BACKGROUND OF THE INVENTION

A number of proteins referred to in the art as bone morphogenetic proteins (BMPs) have recently been identified which are able to induce bone or cartilage formation when implanted into mammals. For example, Wang et at. in U.S. Pat. No. 5,013,649, incorporated herein by reference, describe the DNA sequences encoding bovine and human bone morphogenetic proteins 2A (now bone morphogenetic protein-2) and 2B (now bone morphogenetic protein 4); the corresponding proteins encoded by those DNA sequences, and processes for recombinant production of the BMP-2A (now BMP-2) and BMP-2B (now BMP-4) proteins. Wozney et al., in U.S. Pat. No. 5,106,748, incorporated herein by reference, describe the DNA and amino acid sequences of bovine and human bone morphogenetic protein-5 (BMP-5), along with processes for recombinant production of the BMP-5 proteins. In U.S. Pat. No. 5,187,076, incorporated herein by reference, Wozney et at. disclose DNA sequences, amino acid sequences, and process for recombinant production of human and bovine bone morphogenetic protein-6 (BMP.-6). DNA and amino acid sequences encoding bone morphogenetic protein-7 (BMP-7, sometimes referred to as OP-1 ) and processes for recombinant production of BMP-7 are described in Rosen, et at., U.S. Pat. No. 5,141,905, incorporated herein by reference. DNA sequences encoding BMP-8 are disclosed in PCT publication WO91/18098. DNA sequences encoding BMP-9 are disclosed in PCT publication WO93/00432. These references are herein incorporated by reference. These proteins are expected to have broad medical applicability in treatment of bone and cartilage injuries and disorders in mammals. In order to fulfill the expected medical need for these bone morphogenetic proteins, large quantities of biologically active protein will be needed.

Recombinant production of the bone morphogenetic proteins is possible both in eukaryotic and prokaryotic cell culture systems. A common occurrence in recombinant production of heterologous proteins in prokaryotic cells, such as bacteria, is the formation of insoluble intracellular precipitates known as inclusion bodies. While the bacteria are generally able to transcribe and to translate DNA sequences encoding heterologous proteins correctly, these prokaryotic cells are unable to fold some heterologous proteins sufficiently correctly to allow for their production in a soluble form. This is particularly true of prokaryotic expression of proteins of eukaryotic origin, such as the bone morphogenetic proteins. Formation of incorrectly folded heterologous proteins has to some extent limited the commercial utility of bacterial fermentation to produce recombinant mammalian proteins. When produced in bacteria, the recombinant bone morphogenetic proteins are often similarly found in inclusion bodies in an aggregated, biologically inactive form.

Several methods for obtaining correctly folded heterologous proteins from bacterial inclusion bodies are known. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment which allows correct formation of disulfide bonds (a redox system). General methods of refolding are disclosed in Kohno, Meth. Enzym., 185:187-195 (1990).

EP 0433225 describes a method for refolding transforming growth factor $\beta$ (T6F-$\beta$)-like proteins which employs, in addition to a chaotropic agent and a redox system, a solubilizing agent in the form of a detergent. EP 0433225 predicts that the methods disclosed therein are generally applicable for refolding "TGF-$\beta$-like proteins", based on the degree of homology between members of the TGF-$\beta$ family. However, the present inventors have found that the methods disclosed in EP 0433225 produce undesirably low yields of correctly folded, biologically active dimefie protein when applied to bacterially produced BMP-4, BMP-5, BMP-6, or BMP-7 for unknown reasons.

SUMMARY OF THE INVENTION

It has been found, unexpectedly, that although some bone morphogenetic proteins do not yield correctly folded, biologically active dimeric protein when produced bacterially, such as BMP-4, BMP-5, BMP-6 or BMP-7, certain mutant forms of these proteins are able to yield such proteins. It has further been found, also unexpectedly, that certain mutant forms of bone morphogenefic proteins are also able to yield correctly folded, biologically active heterodimers, such as heterodimers of BMP-2/5 and BMP-2/6, in good quantity, whereas the native forms of these proteins produce undesirably low yields of correctly folded, biologically active heterodimers, yields which are improved by the methods of this invention.

Accordingly, in one embodiment, the invention comprises mutant forms of BMP-4 which are useful in bacterial production processes for yielding correctly folded, biologically active forms of BMP-4.

In another embodiment, the invention comprises mutant forms of BMP-5, BMP-6 and BMP-7 which are useful in bacterial production processes for yielding correctly folded, biologically active forms of heterodimers of BMP-2/5, BMP-2/6 and BMP-2/7.

In a further embodiment, the invention comprises DNA molecules comprising DNA sequences encoding the above mutant forms of bone morphogenetic proteins.

The present invention further comprises a method for obtaining other routants of bone morphogenetic proteins with improved refolding properties, and the mutant proteins thereby obtained.

BRIEF DESCRIPTION OF THE SEQUENCES

SEQ ID NO:1 is the nucleotide sequence encoding BMP-2.

SEQ ID NO:2 is the amino acid sequence for BMP-2.

SEQ ID NO:3 is the nucleotide sequence encoding BMP-4.

SEQ ID NO:4 is the amino acid sequence for BMP-4.

SEQ ID NO:5 is the nucleotide sequence encoding BMP-5.

SEQ ID NO:6 is the amino acid sequence for BMP-5.

SEQ ID NO:7 is the nucleotide sequence encoding BMP-6.

SEQ ID NO:8 is the amino acid sequence for BMP-6.

SEQ ID NO:9 is the nucleotide sequence encoding BMP-7.

SEQ ID NO:10 is the amino acid sequence for BMP-7.

DESCRIPTION OF THE FIGURE

FIG. 1 is a comparison of sequences of BMP-2, 4, 5 6 and 7.

DETAILED DESCRIPTION OF THE INVENTION

In accordance with the present invention, mutant forms of recombinant bone morphogenetic protein-4 (BMP-4)(SEQ ID NO:3 and 4); BMP-5 (SEQ ID NO:5 and 6); BMP-6 (SEQ ID NO:7 and 8); and BMP-7 (SEQ ID NO:9 and 10) may be used to produce large quantifies of BMP homodimers or heterodimers from bacteria and refolded into biologically active dimeric molecules.

The DNA molecules of the present invention include DNA molecules comprising a nucleotide sequence encoding BMP-4, except that the nucleotide triplet encoding glutamic acid at residue 107 (i.e., nucleotides 319 to 321 of SEQ ID NO:3) is replaced (for example, by mutation or synthetically) by a nucleotide triplet that encodes an aspattic acid at residue 107.

Another embodiment of the present invention comprises DNA molecules comprising a nucleotide sequence encoding BMP-5, BMP-6, or BMP-7, except that the nucleotide triplet encoding alanine at residue 56 of BMP-5 or BMP-6 (i.e., nucleotides 166 to 168) of SEQ ID NO:5 or 7), or residue 63 of BMP-7 (i.e., nucleotides 187 to 189 of SEQ ID NO:9) is replaced (for example, by mutation or synthetically) by a nucleotide triplet that encodes a histidine.

The present invention further comprises purified compositions of protein comprising the amino acid sequence of BMP-4, except that the amino acid glutamic acid at residue 107 is replaced by an aspartic acid. This modified BMP-4 protein may be referred to by the nomenclature BMP-4(Δ107Asp).

In another embodiment, the present invention comprises purified compositions of protein comprising the amino acid sequences of BMP-5, BMP-6 or BMP-7, except that the amino acid alanine at residue 56 of BMP-5 or BMP-6, or residue 63 of BMP-7, is replaced by a histidine. The modified BMP-5 protein may be referred to, for example, by the nomenclature BMP-5(Δ56His).

As used herein, the term correlative means the following. It is known that BMP-2 comprises a dimer of polypeptide chains, each of which is 114 amino acids in length. Similarly, BMP-4 comprises a dimer of polypeptide chains, each of which is 116 amino acids in length. BMP-5 and BMP-6 each comprise dimers of polypeptide chains, each of which is 132 amino acids in length. BMP-7 comprises a dimer of polypeptide chains, each of which is 139 amino acids in length. It is further known that the amino acids of BMP-2 from the leucine at residue 19 (correlative to residue 21 of BMP-4) through arginine at residue 114 is highly homologous to BMP-4 from leucine at residue 21 to arginine at residue 116). Similarly, it is known that the amino acids of BMP-2 from leucine 19 of BMP-2 through arginine 114 of BMP-2 are highly homologous to amino acids leucine 36 through histidine 132 of BMP-5 and BMP-6 and amino acids leucine 43 through histidine 139 of BMP-7. Thus, the leucine at residue 19 of BMP-2 is said to be correlative to residue 21 of BMP-4, and to residues 36 of BMP-5 and BMP-6, and to residue 43 of BMP-7. Similarly, the aspartic acid at residue 105 of BMP-2 is said to be correlative to the glutamic acid at residue 107 of BMP-4, and the histidine at residue 39 of BMP-2 is said to be correlative to the aianine at residues 56 of BMP-5 and BMP-6 and the alanine at residue 63 of BMP-7. Alternatively, the 112 amino acid sequence of TGF-β may also be used as a reference point for defining correlative amino acids.

From an examination of FIG. 1, it can be seen that BMP-2 and BMP-4 are highly homologous, beginning at the first cysteine (residue 14 of BMP-2; correlative residue 16 of BMP-4). There are only eight correlative residues which are different. These are, respectively, at residues 15, 39, 46, 73, 95, 96 and 105 of BMP-2. Yet, Applicants have found that the methods disclosed in EP 0433225, which are effective for refolding BMP-2 in acceptable quantities, produce undesirably low yields of correctly folded, biologically active dimeric protein when applied to bacterially produced BMP-4. Applicants constructed molecules in which the first four (N-terminal) of these residues resembled the BMP-2 residue, while the last four (C-terminal) of these residues resembled the correlative BMP-4 residue (called "BMP-2/BMP-4"). Applicants also constructed molecules in which the N-terminal four of these residues resembled BMP-4, while the C-terminal four of these residues resembled the correlative BMP-4 residue (called "BMP-4/BMP-2). As described in Example 2, Applicants found that while BMP-4/BMP-2 refolded in good quantity, BMP-2/BMP-4 did not.

The present invention includes DNA molecules comprising a DNA sequence encoding BMP-4, wherein at least the nucleotide sequence encoding the amino acid glutamic acid at residue 107 is replaced by the correlative nucleotide sequence of BMP-2 encoding aspartic acid. In addition, it is contemplated that other nucleotide sequences of BMP-4 may be replaced by the correlative nucleotide sequence of BMP-2, so long as the glutamic acid residue at 107 is replaced by the correlative aspartic acid residue of BMP-2. Such a DNA molecule may be chimeric, that is, portions of BMP-2 coding sequence and BMP-4 coding sequence may be ligated together through methods readily known to those skilled in the art. Alternatively, this DNA molecule may be constructed synthetically or through mutations, such as by chemical means. The DNA molecule, once formed can be dimerized through methods known in the art, either with itself (homodimer) or with a different member of the BMP family (heterodimer).

The present invention further includes DNA molecules comprising a DNA sequence encoding BMP-5, BMP-6 or BMP-7, wherein the nucleotide sequence encoding the amino acid alanine at residue 56 of BMP-5 or BMP-6, or residue 63 of BMP-7, is replaced by the correlative nucleotide sequence of BMP-2. In addition, it is contemplated that other nucleotide sequences of BMP-5, BMP-6 or BMP-7 may be replaced by the correlative nucleotide sequence of BMP-2, so long as the alanine residue at 56 (63 of BMP-7) is replaced by the correlative histidine residue of BMP-2. Such a DNA molecule may be chimeric, that is, portions of BMP-2 coding sequence and BMP-5, BMP-6 or BMP-7 coding sequence may be ligated together through methods readily known to those skilled in the art. Alternatively, this DNA molecule may be constructed synthetically or through mutations, such as by chemical means. The DNA molecule, once formed can be dimerized through methods known in the art.

The present invention further comprises methods of obtaining other routants of bone morphogenetic proteins (BMP) with improved refolding properties, and the mutant proteins thereby obtained. The method comprises first comparing the amino acid sequence of a BMP which is found to refold well (BMP+) using the refolding methods described herein, with the amino acid sequence of a BMP which does not refold well using such methods (BMP-), and the differences at correlative amino acid positions are determined. Next, the amino acid sequence of BMP- is altered so that one or more aminos acids different from those of correlative amino acids of BMP+ are replaced by the correlative amino acids of BMP+. For example, such modified amino acids could be formed by creating one or more nucleotide mutations or substitutions in the DNA sequence encoding the amino acid sequence for BMP- so that the DNA sequence will express a modified BMP- protein. The modified BMP- protein is then tested for its ability to refold. This method may be repeated for each amino acid position at which the sequence of BMP+ and BMP- differ in order to identify those amino acid residues that are critical to the differences in refolding. Further, multiple changes to the amino acid sequence of BMP- may be made to replace amino acid residues with the correlative amino acid from BMP+ in order to further improve the refolding of the modified BMP protein. The modified BMP- proteins, and the DNA sequence encoding them, are also within the present invention.

Methods of mutagenesis of proteins and nuceleic acids are known, for example see Sambrook et al., *Molecular Cloning:A Laboratory Manual.*, 2d ed. (Cold Spring Harbor, N.Y.: Cold Spring Harbor Laboratory Press)(1990). It is further known that there may exist more than one nucleotide triplet that encodes a given amino acid residue. For example, a histidine residue may be encoded by either CAT or CAC, and an aspartic acid residue may be encoded by either GAT or GAC. See Lehninger, Biochemistry, (Worth Publishers, N.Y., N.Y.)

Any bacterial species may be used to generate recombinant BMP for refolding in the method of the invention. Preferably, *Bacillus subtilis* is used to produce inclusion bodies containing BMP. More preferably, *Pseudomonas* is used to produce inclusion bodies containing BMP for refolding in the method of the invention. Most preferably, *Escherichia coli* is used to produce inclusion bodies containing BMP for refolding in the method of the invention. Any strain of *E. coli* may be used to produce BMP for refolding in the method of the invention, so long as that strain is capable of expression of heterologous proteins. One preferred strain, *E. coli* strain GI724 (A.T.C.C. accession number 55151) may be used to produce BMP for refolding in the method of the invention.

The mutant forms of BMP of the present invention may be produced in bacteria using known methods. It may be necessary to modify the N-terminal sequences of the mutant forms of BMP in order to optimize bacterial expression. For example, because cleavage of the bond between formyl-methionine and glummine is inefficient in *E. coli*, the N-terminus of the native mature BMP-2 protein (Met-gln-ala-lys) is modified by deletion of the glummine residue to yield an N-terminus more suitable for BMP-2 production in *E. coli* (Met-ala-lys-his). Other bacterial species may require analogous modifications to optimize the yield of the mutant BMP obtained therefrom. Such modifications are well within the level of ordinary skill in the art.

The modified or unmodified nucleotide sequence of SEQ ID NO:3 which encodes BMP4; SEQ ID NO:5 ID NO:5, which encodes BMP-5; SEQ ID NO:7, which encodes BMP-6; or SEQ ID NO:9, which encodes BMP-7, may be inserted into a plasmid suitable for transformation and expression of those heterologous proteins in bacteria. Any bacterial expression plasmid may be used, so long as it is capable of directing the expression of a heterologous protein such as BMP in the bacteria chosen. Acceptable species of bacteria include *B. subtilis*, species of *Pseudomonas*, and *E. coli*. Suitable expression plasmids for each of these species are known in the art. For production of BMP in bacteria, a suitable vector is described in Taniguchi et al., PNAS:USA, 77:5230–5233 (1980).

The bacterial expression plasmid may be transformed into a competent bacterial cell using known methods. Transformants are selected for growth on medium containing an appropriate drug when drug resistance is used as the selective pressure, or for growth on medium which is deficient in an appropriate nutrient when auxotrophy is used as the selective pressure. Expression of the heterologous protein may be optimized using known methods. The BMP thus obtained will be present in insoluble, refractile inclusion bodies which may be found in pellets of disrupted and centrifuged cells.

The inclusion bodies thus obtained are then solubilized using a denaturant or by acidification with acetic acid or trifluoroacetic acid. If solubilized using a denaturant, a reducing agent such as β-mercaptoethanol or dithiothreitol is added with the denaturant. If the protein is solubilized by acidification, it must be reduced prior to acidification. The solubilized heterologous protein may be further purified using known chromatographic methods such as size exclusion chromatography, or exchange chromatography, or reverse phase high performance liquid chromatography.

The solution containing the BMP is then reduced in volume or vacuum desiccated to remove chromatography buffer, and redissolved in medium [suitable media include 50 mM Tris, 1.0 M NaCl, 2% 3-(3-chlolamidopropyl)dimethylammonio-1-propane-sulfate (CHAPS), 5 mM EDTA, 2 mM gluatathione (reduced) 1 mM glutathione (oxidized); at pH of approximately 8.5; other media which may be suitable for redissolution include alternative refolding buffers described elsewhere in the specification (e.g., guanidine, urea, arginine)] to yield a concentration of 1 to 100 µg/ml protein. Higher concentrations of protein may be refolded in accordance with the invention, for example up to about 1 mg/ml, but precipitates or aggregates are present above protein concentrations of 100 µg/ml and the yield of active BMP homodimer or heterodimer may be decreased accordingly.

For production of heterodimers, the above procedure is performed utilizing equal amounts of two plasmids, each containing a coding sequence for a distinct BMP (e.g., pALBP2, encoding BMP-2 and pALBPX encoding BMP-X, where X is 5, 6 or 7). The plasmids are cultured separately, and the resulting inclusion bodies are solubilized and refolded in accordance with the methods described herein. The refolded protein monomers are mixed together in equivalent ratios and treated as described in the paragraph above. For heterodimers, the media uses CHAPS as the refolding buffer. The resulting dimeric promins are observed to include homodimers of BMP-2, as well as heterodimers of BMP-2/X. These species may be separated out from each other through procedures known in the art.

In order to refold the proteins, the following conditions and media may be used: 50 mM Tris, 1.0 M NaCl, 2% 3-(3-chlolamido-propyl)dimethylammonio-1-propane-sulfate (CHAPS), 5 mM EDTA, 2 mM gluatathione (reduced) 1 mM glutathione (oxidized); at pH of approximately 8.5. With minor modifications, other detergents, including non-ionic, e.g. digitonin, or zwitterionic detergents, such as 3-(3-chlolamidopropyl)-dimethylammonio-1-propanesulfonate (CHAPSO), or N-octyl glucoside, may be used in the present invention. One skilled in the art will recognize that the above conditions and media may be varied, for example, as described below. Such variations and modifications are within the present invention.

Because BMPs are disulfide bonded dimers in their active state, it is useful to include a redox system which allows formation of thiol/disulfide bonds in the method of the invention. Several such redox systems are known. For example the oxidized and reduced forms of glutathione, dithiothreitol, β-mercaptoethanol, β-mercaptomethanol, cystine and cystamine may be used as redox systems at ratios of reductant to oxidant of about 1:10 to about 2:1. When the glutathione redox system is used, the ratio of reduced glutathione to oxidized glutathione is preferably 0.5 to 5; more preferably 1 to 1; and most preferably 2 to 1 of reduced form to oxidized form.

With additional modifications, other refolding agents, such as urea, guanidine, arginine and other means of refolding, may be useful in order to produce correctly refolded proteins with the routants of the present invention. Chaotropic agents are generally used at concentrations in the range of 1 to 9 M. When urea is the refolding agent, it is preferably present at concentrations in the range of about 0.1 M to about 3 M, more preferably about 0.5 M to 2.5 M, or about 1.0 M to about 2.0 M.

When guanidine hydrochloride is used as the refolding agent, it is preferably initially added at high concentrations, for example, 7–8 M, and then the concentration of guanidine is reduced to induce refolding. The reduction of guanidine concentration may occur instantaneously, as by dilution, or gradually, as by dialysis. Preferably the guanidine concentration is reduced to a final concentration of less than about 1.5 M, or more preferably less than about 1 M. When the guanidine concentration is reduced gradually, the guanidine may be completely removed from the refolded protein. Dilution of a guanidine is preferable over dialysis.

When arginine is used as the refolding agent, it is preferably present at concentrations of about 0.4 M to about 1.5 M, more preferably, about 0.6 M to about 1.25 M, or about 0.6 M to about 1.0 M.

In addition to the refolding agent, the method of the invention may employ a salt moiety. When detergents, such as CHAPS, are used, the salt moiety is preferably NaCl, preferably at a concentration of about 0.5 M to about 2.0 M, preferably about 1.0 M. When urea is the refolding agent, the salt moiety is preferably sodium chloride, preferably at a concentration of about 0.25 M to about 2 M. More preferably, the sodium chloride is present at a concentration in the range of about 0.5 M to about 1.5 M when urea is the refolding agent. Most preferably, when urea is the refolding agent, sodium chloride is present at a concentration in the range of about 0.75 M to about 1.25 M. When guanidine is used as the refolding agent, the sodium chloride concentration must be increased as the concentration of guanidine increases. For example, for refolding in 0.2 M guanidine, the range of NaCl concentration which is optimal is 0.25 to 0.5 M, while for refolding in 1.0 M guanidine, 1.0 to 2.0 M NaCl is necessary for optimal refolding.

The pH of the refolding reaction of the present invention when urea is the refolding agent is preferably from about 7.5 to about 11; more preferably from about 8.5 to about 10.5. When detergents such as CHAPS, are used as the refolding agent, the preferred pH is about 8.5. When guanidine is used as the refolding agent, the pH is preferably from about 7.5 to about 9.5; more preferably about 8.5; and most preferably about 9.5. When arginine is used as the refolding agent, the pH is preferably from about 8 to about 10; more preferably from about 8.5 to about 10; and most preferably from about 9.5 to about 10.

Preferably, the refolding reaction of the invention is performed at a temperature range from about 4° C. to about 23° C. More preferably, the refolding reaction is performed at 4° C. The refolding reactions of the present invention are allowed to proceed to completion, preferably about 16 hours.

The extent of refolding of bone morphogenetic proteins obtained is monitored by sodium dodecyl sulfate-polyacrylamide electrophoresis (SDS-PAGE) under non-reduced and reduced conditions. The BMP-4 homodimer will appear as a band of about 30 kD under non-reduced conditions on a 16 percent SDS-polyacrylamide gel; and the BMP-4 monomer appears as a band of about 13 kD under reduced conditions. The BMP-2/5 heterdimer will appear as a band of about 35 kD under non-reduced conditions on a 16 percent SDS-polyacrylamide gel; the BMP-2 monomer appears as a band of about 13 kD under reduced conditions; and the BMP-5 monomer appears as a band of about 15 kD under reduced conditions. The BMP-2/6 heterodimer will appear as a band of about 35 kD under non-reduced conditions on a 16 percent SDS polyacrylamide gel; the BMP-2 monomer appears as a band of about 13 kD under reduced conditions; and the BMP-6 monomer appears as a band of about 15 kD under reduced conditions. The BMP-2/7 heterodimer will appear as a band of about 35 kD under non-reduced conditions on a 16 percent SDS-polyacrylamide gel; the BMP-2 monomer appears as a band of about 13 kD under reduced conditions; and the BMP-7 monomer appears as a band of about 15 kD under reduced conditions.

The in vitro biological activity of the refolded bone morphogenetic proteins is monitored by the W-20 assay as set forth in Example 9. Use of the W-20-17 bone marrow stromal cells as an indicator cell line is based upon the conversion of these cells to osteoblast-like cells after treatment with BMP [R. S. Thies et at., Journal of Bone and Mineral Research 5(2):305 (1990); and R. S. Thies et al., Endocrinology 130:1318–1324 (1992)]. W-20-17 cells are a clonal bone marrow stromal cell line derived from adult mice by researchers in the laboratory of Dr. D. Nathan, Children's Hospital, Boston, Mass. Treatment of W-20-17 cells with BMP results in (1) increased alkaline phosphatase production, (2) induction of parathyroid hormone stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date the conversion of W-20-17 stromal cells to osteoblast-like cells has been observed only upon treatment with bone morphogenetic proteins. The in vivo biological activity of the refolded bone morphogenetic proteins is monitored by a modified version of the rat bone formation assay described in Sampath and Reddi, Proc. Natl. Acad. Sci. USA, 80:6591–6595 (1983) herein called the Rosen-modified Sampath-Reddi assay, as set forth in Example 10.

EXAMPLE 1

Refolding of BMP-4 using CHAPS System 1.0 g of cells stored at −80° C. are measured. Solution (3.4 ml 100 mM TRIS, 10 mM EDTA, pH 8.5) is added. The solution is vortexed until cells are well suspended. 40 µl 100 mM PMSF in isopropanol is added. The cells are lysed at 1000 psi in a French pressure cell. The inclusion bodies are centrifuged at 4° C. for 20 minutes in an Eppendorf microfuge to form pellets. The supernatants are decanted. To one pellet (out of 4 total) 1.0 ml degassed 8.0 M guanidine hydrochloride, 0.5 M TRIS, 5 EDTA, pH 8.5, containing 250 mM DTT is added. The pellet is dissolved and argon is blown over the liquid for 30 seconds. Next the solution is incubated at 37° C. for one hour. Insoluble material is pelleted for 2–3 minutes in an Eppendorf microfuge at 23° C. 0.5–1.0 ml of supernatant is injected onto a Supelco 2 cm guard cartridge (LC-304), and eluted with an acetonitrile gradient in 0.1% TFA from 1–70% over 35 minutes. BMP-4 elutes between 30 and 32 minutes. Fractions are pooled and the protein concentration determined by A280 versus 0.1% TFA, using the theoretical extinction coeffecient based upon the amino acid content.

A sufficient volume of the BMP-4 pool is lyophilized to give 10 µg of protein. 5 µl of glass distilled water is added to redissolve the residue, then 100 µl of refold mix (TRIS, salt, CHAPS, etc.) is added. The solution is gently mixed and stored at 23° C. for 1–4 days. Dimer formation is assessed by running an aliquot on a Novex 16% tricine gel at 125 volts for 2.5 hours, followed by Coomassie Blue staining and destaining.

EXAMPLE 2

Refolding of other BMP dimers

From an examination of FIG. 1, it can be seen that BMP-2 and BMP-4 are highly homologous, beginning at the first cysteine (residue 14 of BMP-2; correlative residue 16 of BMP-4). There are only eight correlative residues which are different. These are, respectively, at residues 15, 39, 46, 73, 95, 96 and 105 of BMP-2. Yet, Applicants have found that BMP-4 that the methods disclosed in EP 0433225, which are effective for refolding BMP-2 in acceptable quantities, produce undesirably low yields of correctly folded, biologically active dimeric protein when applied to bacterially produced BMP-4. Applicants constructed molecules in which the first four (N-terminal) of these residues resembled the BMP-2 residue, while the last four (Cterminal) of these residues resembled the correlative BMP-4 residue (called "BMP-2/BMP-4"). Applicants also constructed molecules in which the N-terminal four of these residues resembled BMP-4, while the C-terminal four of these residues resembled the correlative BMP-4 residue (called "BMP-4/BMP-2"). These molecules were worked up as described for wild-type BMP-4 above.

Gels were run with the appropriate control proteins (e.g., the BMP-4 routants next to wild-type BMP-4; BMP-2 and wild-type BMP-5 mixed together as a control for the BMP-2 and BMP-5(Δ56His).

Wild-type BMP-4 did not refold well. While BMP-4/BMP-2 refolded in good yield; however, BMP-2/BMP-4 does not. BMP-4(Δ107 Asp) homodimer refolds in good quantity relative to wild-type BMP-4.

BMP-2/BMP-5 heterodimer does not refold well. BMP2/BMP5(Δ56 HIS) heterodimer refolds in good quantity relative to BMP-2/BMP-5.

BMP-2/BMP-6 heterodimer does not refold well. BMP2/BMP6(Δ56 His) heterodimer refolds in good quantity relative to BMP-2/BMP-6.

EXAMPLE 3

Expression of BMP in *E. coli*

An expression plasmid pALBP2-782 containing the following principal features was constructed for production of BMP-2 in *E. coli*. Nucleotides 1-2060 contain DNA sequences originating from the plasmid pUC-18 [Norrander et al., Gene 26:101–106 (1983)] including sequences containing the gene for β-lactamase which confers resistance to the antibiotic ampicillin in host *E. coli* strains, and a colE1-derived origin of replication. Nucleotides 2061-2221 contain DNA5 sequences for the major leftward promotor (pL) of bacteriophage λ [Sanger et al., J. Mol. Biol. 162:729–773 (1982)], including three operator sequences $O_L1$, $O_L2$ and $O_L3$. The operators are the binding sites for λcI repressor protein, intracellular levels of which control the amount of transcription initiation from pL. Nucleotides 2222–2723 contain a strong ribosome binding sequence included on a sequence derived from nucleotides 35566 to 35472 and 38137 to 38361 from bacteriophage lambda as described in Sanger et al., J. Mol. Biol. 162:729–773 (1982). Nucleotides 2724–3133 contain a DNA sequence encoding mature BMP-2 protein with an additional 62 nucleotides of 3′-untranslated sequence. Nucleotides 3134–3149 provide a "Linker" DNA sequence containing restriction endonuclease sites. Nucleotides 3150–3218 provide a transcription termination sequence based on that of the *E. coli* asp A gene [Takagi et al., Nucl. Acids Res. 13:2063–2074 (1985)]. Nucleotides 3219–3623 are DNA sequences derived from pUC-18.

Using restriction endonucleases and procedures known in the art, one can readily replace the coding sequence for BMP-2 contained in pALBP2-781 with the coding sequence for another BMP desired to be produced in *E. coli*. With this substitution in the pALB2-781 plasmid, the following examples may be used to express and refold any of the BMPs of the present invention.

Plasmid pALBP2-781 was transformed into the *E. coli* host strain GI724 (F,lacI$^q$, lacp$^{L8}$, ampC::λcI$^+$) by the procedure of Dagert and Ehrlich, Gene 6:23 (1979). GI724 (ATCC accession No. 55151) contains a copy of the wild-type λcI repressor gene stably integrated into the chromosome at the ampC locus, where it has been placed under the transcriptional control of *Salmonella typhimurium* trp promotor/operator sequences. In GI724, λCI protein is made only during growth in tryptophan-free media, such as minimal media or a minimal medium supplemented with casamino acids such as IMC, described above. Addition of tryptophan to a culture of GI724 will repress the trp promoter and turn off synthesis of λcI, gradually causing the induction of transcription from pL promoters if they are present in the cell.

Transformants were selected on 1.5% w/v agar plates containing IMC medium, which is composed of M9 medium [Miller, "Experiments in Molecular Genetics," Cold Spring Harbor Laboratory, New York (1972)] supplemented with 1 mM MgSO4, 0.5% w/v glucose, 0.2% w/v casamino acids and 100μg/ml ampicillin and the culture incubated for a further 4 hours on ampicillin-containing medium. During this time BMP protein accumulates to approximately 10% of the total cell protein, all in the "inclusion body" fraction.

Nine grams of frozen cell pellets obtained from the *E. coli* transformants as described above were thawed in 30 ml of TE8.3(100:10) buffer (100 mM Tris-HCl pH 8.3, 10 mM Na2EDTA, 1 mM phenylmethylsulfonyl fluoride [PMSF]). Cells were lysed by three passes through a Microfluidizer ™ [model #MCF 100 T]. The lysate was diluted to approximately 120 ml with TE8.3 100:10 buffer. A pellet of inclusion body material was obtained by centrifugation at 15,000×g. The supernatant was decanted, and the inclusion body material was suspended in 50 ml TE8.3(100:10) which also contained 1% Triton-X100. The resuspended inclusion bodies were centrifuged for 10 minutes at 15,000×g, and the supernatant was decanted. The pellet was suspended in TE8.3(20:1) buffer (20 mM Tris-HCl pH 8.3, 1 mM Na2EDTA, 1 mM PMSF) which also contained 1% dithiothrietol [DTT]. After the suspension was homogenized in a Wheaton glass homogenizer, it was acidified to pH 2.5 with glacial acetic acid and then centrifuged 25 minutes at 15,000×g. The supernatant from this centrifugation was collected and chromatographed over a Sepharose S-100 ™ size exclusion column (83 cm×2.6 cm; ≈440 ml bed) in 20 ml increments. The Sepharose S-100 ™ column was run with a mobile phase of 1% acetic acid at a flow rate of 1.4 ml/min. Fractions corresponding to BMP-2 monomer were detected by absorbance at 280 nm, and using a computer calculated extinction coefficient of 18200 $M^{-1}cm^{-1}$ and molecular weight (12777 daltons). This size exclusion column pooled material was used as starting material for refolding reactions.

Alternatively, cells were lysed as above, but the initial inclusion body material pellet was dissolved in 8 M guanidine-HCl, TE8.5(100:10) buffer (100 mM Tris-HCl pH 8.5, 10 mM Na2EDTA which contained 100 mM DTT, and incubated at 37° C. for 1 hour. This material was centrifuged at 12,000×g for 15 minutes at room temperature. The supernatant was injected onto C4 analytical RP-HPLC (reversed phase-high performance liquid chromatography) column (Vydac 214TP54) equilibrated to 1% B buffer (A buffer-0.1% trifluoroacetic acid, B buffer=95% acetonitrile, 0.1% trifluoroacetic acid [TFA]), with a flow rate of 1 ml/min. After 5 minutes, a linear gradient from 1% to 70% B buffer (diluted into A buffer) was run over 35 minutes, during which time the protein elutes. Protein was monitored by absorbance at 280 nm. Peak BMP-2 fractions (eluting between 25 and 35 minutes) were pooled. The concentration was determined by absorbance at 280 nm, and using the computer calculated extinction coefficient and molecular weight as indicated above. This RP-HPLC C4 Column pooled material was also used as starting material for refolding reactions.

EXAMPLE 4

Refolding of *E. coli* Produced BMP-2 in Urea/NaCl

BMP-2 protein in 1% acetic acid or in reverse phase buffer containing 0.1% TFA, 30-40% acetonitrile was dried or reduced in volume using a speed vacuum, re, dissolved with a few microliters of 0.01% TFA, and allowed to dissolve completely for 5 to 10 minutes. A buffer containing 7 M to 8 M urea, 100 mM 2-(N-cyclohexylamino)-ethanesulfonic acid [CHES] pH 9.5, 5 mM EDTA was added to the BMP-2 in TFA and allowed to incubate for 20 minutes at room temperature (RT, approximately 23° C.) before dilution. The protein concentrations used were such that the final BMP-2 concentration in the diluted state was 10 to 100 μg/ml. The final conditions of the folding buffer contained 100 mM CHES, 5 mM EDTA, and the desired concentration of salt for the urea concentration used. Several ranges of urea, NaCl, pH, and redox conditions were tested to optimize BMP-2 refolding conditions.

Refolding of the *E. coli* produced BMP-2 in urea/NaCl was analyzed under reducing and non-reducing conditions using 16% Tricine-sodium dodecyl sulfate polyacrylamide electrophoresis (SDS-PAGE).

Refolding was scored as positive when the BMP-2 appeared as a dimer of the appropriate molecular weight under non-reducing conditions and as a monomer of appropriate molecular weight under reducing conditions. Yield of refolded BMP-2 was determined by scanning bands on loomassie blue or silver stained gels. Biological activity of the refolded BMP-2 dimer was tested using the assays of Examples 9 and 10 below.

Refolding of *E. coli* produced BMP-2 in urea and NaCl optimally occurred at ranges of 1.0 to 2.0 M urea and 0.75 to 1.25 M NaCl. SDS-PAGE bands of medium intensity were observed within concentration ranges of 0.5 to 1.0 M and 2.0 to 2.5 M urea and 0.5 to 0.75 M and 1.25 to 1.5 M NaCl. Faint bands corresponding to refolded BMP-2 were observed to occur at concentrations in ranges of 0.1 to 0.5 and 2.5 to 3 M urea and 0.25 to 0.5 and 1.5 to 2 M NaCl. Refolding of BMP-2 occurred within the pH range of 7.5 to 11, with better refolding in the pH range of 8.5 to 10.5 and optimal refolding in the pH range of 9 to 10.

EXAMPLE 5

Refolding of *E. coli* Produced BMP-2 in Guanidine/NaCl

BMP-2 protein in 1% acetic acid or in reverse phase buffer of 0.1% TFA, 3-40% acetonitrile was dried or reduced in volume to remove acetonitrile using a speed vacuum, redissolved with four microliters 0.01% TFA and allowed to dissolve completely for 5 to 10 minutes. A solution containing 8 M to 8.5 M guanidine HCl (guanidine), 100 mM CHES pH 9.5, 5 mM EDTA was added to the BMP-2 in TFA and allowed to incubate for 20-30 minutes at room temperature before dilution. The protein concentrations used were such that the final protein concentration in the diluted state was 10 to 100 λg/ml.

The guanidine/BMP solution was diluted into a chilled folding buffer (on ice) with the appropriate amount of NaCl and with 50-100 mM CHES pH 9.5, 5 mM EDTA, 2 mM reduced glutathione (GSH), 1 mM oxidized glutathione (GSSG). Samples were argon bubbled (15 seconds) while on ice, and incubated at 4° C.

Refolding of the *E. coli* produced BMP-2 in guanidine was analyzed under reducing and non-reducing conditions using Tricine-SDS-PAGE as described above in Example 4.

Refolding of *E. coli* produced BMP-2 in guanidine optimally occurred at ranges of 0.18 to 1.0 M guanidine. SDS-PAGE bands of medium intensity were observed within concentration ranges of 0 to 0.18 M and 1.0 to 1.25 M guanidine. Faint bands corresponding to refolded BMP-2 were observed to occur at concentrations in ranges of 1.25 to 1.5 M guanidine. Refolding of BMP-2 occurred in guanidine within the pH range of 7.5 to 9.5, with better refolding at pH 8.5 and optimal refolding at pH 9.5. Refolding of BMP-2 was optimal at 4° C, though some refolding was observed at room temperature. (approximately 23° ).

EXAMPLE 6

Refolding of *E. coli* BMP-2 in Arginine/NaCl

BMP-2 protein in 1% acetic acid or in reverse phase buffer of 0.1% TFA, 3–40% acetonitrile was dried or reduced in volume to remove acetonitrile using a speed vacuum, redissolved with four microliters of 0.01% TFA and allowed to dissolve completely for 5 to 10 minutes. The protein concentrations used were such that the final protein concentration in the folding buffer was 10 to 100 µg/ml. The folding buffer contained 100 mM buffer titrated to the appropriate pH, 5 mM EDTA, and the desired concentration of salt. Refolding of the *E. coli* produced BMP-2 in arginine was analyzed under reducing and non-reducing conditions using Tricine-SDS-PAGE as described above in Example 4. Substantial bands were observed at all concentrations of arginine used to refold BMP-2; however, the greatest yield of BMP-2 was obtained using 0.6 to 0.8 M arginine and from 0 to 0.25 M NaCl. Several types of salt were tested for ability to enhance BMP-2 refolding: NaCl, $MgCl_2$, $MgSO_4$, $Na_2SO_4$. Of these, NaCl and $MgCl_2$ yielded optimal amounts of refolded BMP-2, and $MgSO_4$ yielded intermediate amounts of refolded BMP-2. The optimal pH range for refolding BMP-2 in arginine is pH 9.5 to 10. Refolding also occurred at pH 8.5. Refolding BMP-2 in arginine was optimal at 4°, though some refolding was observed at room temperature (approximately 23°).

EXAMPLE 7

Refolding of BMP-2 Using Organic Alcohols

Denatured, monomeric BMP-2 (and BMP-6) in 1% acetic acid, prepared as previously described, were added to an Eppendorf tube and lyophilized to dryness. The pellets were redissolved in 20 ul of 0.01% trifluoroacetic acid. 500 ul of buffer was then added, containing 50 mM Tris (pH 8.5), 5 mM EDTA, 1.0 M NaCl, 2 mM reduced glutathione, 1 mM oxidized glutathione, and 10–20% methanol, ethanol, or isopropanol. Samples were incubated at room temperature for three days, the evaluated for dimer formation by SDS-PAGE on a 16% Novex tricine gel. A small but discernible amount of BMP-2 dimer was detected after staining with silver. There was no evidence of any BMP-2/6 heterodimer of BMP 6/6 homodimer on the same gels.

EXAMPLE 8

Purification of Dimeric BMP-2

Urea refolded BMP-2 protein was injected onto a HPLC C4 analytical column (Vydac 214TP54) equilibrated to 10% B buffer (A buffer=0.1% TFA, B buffer=95% acetonitrile, 0.1% TFA), with a flow rate of 1 ml/min. After 15 minutes, a linear gradient from 10% to 50% B buffer was applied over 40 minutes, during which time the dimeric BMP-2 protein eluted. Protein was monitored by absorbance at 280 nm. Peak BMP-2 dimer fractions (eluting between 45 and 48 minutes) were pooled, analyzed by 16% Tricine-SDS-PAGE, and tested for biological activity in the assays described in Examples 9 and 10.

EXAMPLE 9

W-20 Alkaline Phosphatase Assay Protocol

W-20-17 cells are plated into 96 well tissue culture plates at a density of 10,000 cells per well in 200 µl of medium (DME with 10% heat inactivated fetal calf serum, 2 mM glutamine). The cells are allowed to attach overnight in a 95% air, 5% $co_2$ incubator at 37°C.

The 200 µl of medium is removed from each well with a multichannel pipettor and replaced with an equal volume of test sample delivered in DME with 10% heat inactivated fetal calf serum, 2 mM glutamine and 1% penicillin-streptomycin.

The test samples and standards are allowed a 24 hour incubation period with the W-20-17 indicator cells. After the 24 hours, plates are removed from the 37° C. incubator and the test media are removed from the cells.

The W-20-17 cell layers are washed three times with 200 µl per well of calcium/magnesium free phosphate buffered saline and these washes are discarded.

50 µl of glass distilled water is added to each well and the assay plates are then placed on a dry ice/ethanol bath for quick freezing. Once frozen, the assay plates are removed from the dry ice/ethanol bath and thawed at 37° C. This step is repeated two more times for a total of 3 freeze-thaw procures. Once complete, the membrane bound alkaline phosphatase is available for measurement.

50 µl of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute.

At the end of the 30 minute incubation, the reaction is stopped by adding 100 µl of 0.2 n NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

Absorbance Values for Known Standards of P-Nitrophenol Phosphate

| P-nitrophenol Phosphate µmoles | Mean Absorbance (405 nm) |
|---|---|
| 0.000 | 0 |
| 0.006 | 0.261 ± .024 |
| 0.012 | 0.521 ± .031 |
| 0.018 | 0.797 ± .063 |
| 0.024 | 1.074 ± .061 |
| 0.030 | 1.305 ± .083 |

Absorbance values for known amounts of BMP-2 can be determined and converted to µmoles of p-nitrophenol phosphate cleaved per unit time as shown in Table II.

TABLE II

Alkaline Phosphatase Values for W-20 Cells Treated with BMP-2

| BMP-2 concentration ng/ml | Absorbance Reading 405 nmeters | umoles substrate per hour |
|---|---|---|
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.08 |

These values are then used to compare the activities of known amounts of BMP heterodimers to BMP-2 homodimer.

EXAMPLE 10

Rosen-Modified Sampath-Reddi Assay

The ethanol precipitation step of the Sampath-Reddi procedure, supra, is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matfix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [see, A. H. Reddi, et at., Proc. Natl. Acad. Sci., 69:1601 (1972)]

The other half of each implant is fixed and processed for histological analysis. One μm glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 40%, 30%, 20% and 10% respectively of the implant contains new cartilage and/or bone.

We claim:

1. A recombinant DNA molecule comprising a nucleotide sequence encoding BMP-4 as shown in SEQ ID NO:3, except that the nucleotide triplet at 319 to 321 has been replaced with a triplet encoding aspartic acid.

2. A recombinant DNA molecule comprising a nucleotide sequence encoding BMP-5 as shown in SEQ ID NO:5, except that the nucleotide triplet at 166 to 168 has been replaced with a triplet encoding histidine.

3. A recombinant DNA molecule comprising a nucleotide sequence encoding BMP-6 as shown in SEQ ID NO:7, except that the nucleotide triplet at 166 to 168 has been replaced with a triplet encoding histidine.

4. A recombinant DNA molecule comprising a nucleotide sequence encoding BMP-7 as shown in SEQ ID NO:9, except that the nucleotide triplet at 187 to 189 has been replaced with a triplet encoding histidine.

5. A purified mutant BMP-4 comprising the amino acid sequence of SEQ ID NO:4, wherein the glutamic acid at amino acid residue 107 has been replaced with aspartic acid.

6. A purified BMP heterodimer comprising one chain from BMP-2 and one chain from the mutant BMP according to claim 5.

7. A purified mutant BMP-5 comprising the amino acid sequence of SEQ ID NO:6, wherein the alanine at amino acid residue 56 has been replaced with histidine.

8. A purified BMP heterodimer comprising one chain from BMP-2 and one chain from the mutant BMP according to claim 7.

9. A purified mutant BMP-6 comprising the amino acid sequence of SEQ ID NO:8, wherein the alanine at amino acid residue 56 has been replaced with histidine.

10. A purified BMP heterodimer comprising one chain from BMP-2 and one chain from the mutant BMP according to claim 9.

11. A purified mutant BMP-7 comprising the amino acid sequence of SEQ ID NO:10, wherein the alanine at amino acid residue 63 has been replaced with histidine.

12. A purified BMP heterodimer comprising one chain from BMP-2 and one chain from the mutant BMP according to claim 11.

* * * * *